United States Patent
Izatt et al.

(10) Patent No.: US 7,742,174 B2
(45) Date of Patent: Jun. 22, 2010

(54) METHODS, SYSTEMS AND COMPUTER PROGRAM PRODUCTS FOR REMOVING UNDESIRED ARTIFACTS IN FOURIER DOMAIN OPTICAL COHERENCE TOMOGRAPHY (FDOCT) SYSTEMS USING CONTINUOUS PHASE MODULATION AND RELATED PHASE MODULATORS

(75) Inventors: Joseph A. Izatt, Raleigh, NC (US); Eric L. Buckland, Hickory, NC (US); David J. Hamo, Raleigh, NC (US)

(73) Assignee: Bioptigen, Inc., Durham, NC (US)

( * ) Notice: Subject to any disclaimer, the term of this patent is extended or adjusted under 35 U.S.C. 154(b) by 327 days.

(21) Appl. No.: 11/778,854

(22) Filed: Jul. 17, 2007

(65) Prior Publication Data
US 2008/0013093 A1 Jan. 17, 2008

Related U.S. Application Data

(60) Provisional application No. 60/831,375, filed on Jul. 17, 2006.

(51) Int. Cl.
*G01B 9/02* (2006.01)
*G01B 11/02* (2006.01)
*G01J 3/45* (2006.01)

(52) U.S. Cl. ..................... 356/497; 356/456
(58) Field of Classification Search ............. 356/456, 356/479, 497
See application file for complete search history.

(56) References Cited

U.S. PATENT DOCUMENTS

| 6,377,349 | B1 | 4/2002 | Fercher | |
|---|---|---|---|---|
| 7,301,644 | B2 | 11/2007 | Knighton et al. | |
| 7,365,858 | B2 * | 4/2008 | Fang-Yen et al. | 356/489 |
| 7,557,929 | B2 * | 7/2009 | Fang-Yen et al. | 356/484 |
| 2002/0196446 | A1 | 12/2002 | Roth et al. | |
| 2004/0239938 | A1 * | 12/2004 | Izatt | 356/450 |
| 2005/0018201 | A1 | 1/2005 | de Boer et al. | |
| 2005/0057756 | A1 * | 3/2005 | Fang-Yen et al. | 356/497 |
| 2005/0105097 | A1 * | 5/2005 | Fang-Yen et al. | 356/497 |

(Continued)

FOREIGN PATENT DOCUMENTS

EP 1 780 530 A1 5/2007

(Continued)

OTHER PUBLICATIONS

International Search Report, PCT/US2007/016146, Feb. 14, 2008.

(Continued)

*Primary Examiner*—Patrick J Connolly
(74) *Attorney, Agent, or Firm*—Myers Bigel Sibley & Sajovec

(57) ABSTRACT

Methods, fourier domain optical coherence tomography (FDOCT) interferometers and computer program products are provided for removing undesired artifacts in FDOCT systems using continuous phase modulation. A variable phase delay is introduced between a reference arm and a sample arm of an FDOCT interferometer using continuous phase modulation. Two or more spectral interferograms having different phase delay integration times are generated. The spectral interferograms are combined using signal processing to remove the undesired artifacts. Systems and methods for switching between stepped and continuous phase shifting Fourier domain optical coherence tomography (FDOCT) and polarization-sensitive optical coherence tomography (PSOCT) are also provided herein.

41 Claims, 6 Drawing Sheets

U.S. PATENT DOCUMENTS

2006/0072424 A1  4/2006  Everett et al.
2006/0232783 A1* 10/2006 Choma et al. ............... 356/479
2007/0002327 A1  1/2007  Zhou et al.
2007/0291277 A1  12/2007 Everett et al.

FOREIGN PATENT DOCUMENTS

WO    WO 2008/016434 A1    2/2008

OTHER PUBLICATIONS

Invitation to Pay Additional Fees for PCT/US2007/016146; Dec. 3, 2007.
Tao et al. "Complex Conjugate Resolved Retinal SDOCT using Integrating Buckets" *Proc. of SPIE 6429*:6429W-1-6429W-4 (2007).
Yasuno et al. "Simultaneous *B-M*-mode scanning method for real-time full-range Fourier domain optical coherence tomography" *Applied Optis* 45(8):1861-1865 (2006).
Bhushan, Bharat, et al., "Measurement of surface topography of magnetic tapes by Mirau interferometry," Applied Optics, vol. 24, No. 10, May 15, 1985, p. 1489-1497.
Dubois, A., et al., "Sinusoidally phase-modulated interference microscope for high-speed high-resolution topographic imagery," Optics Letters, vol. 26, No. 23, Dec. 1, 2001, p. 1873-1875.
Dubois, Arnold, "Phase-map measurements by interferometry with sinusoidal phase modulation and four integrating buckets," J. Opt. Soc. Am. A, vol. 18, No. 8, Aug. 2001, p. 1972-1979.
Roth et al., "Simplified method for polarization-sensitive optical coherence tomography," Optics Letters, vol. 26, No. 14, Jul. 15, 2001, p. 1069-1071.
Sarunic, M.V., et al., "Real Time Quadrature Projection Complex Conjugate Resolved Fourier Domain Optical Coherence Tomography," Optics Letters 31:2426-2428, 2006.
Wyant, J.C., "Use of an ac heterodyne lateral shear interferometer with real-time wavefront correction systems," Applied Optics, vol. 14, No. 11, Nov. 1975, p. 2622-2626.

* cited by examiner

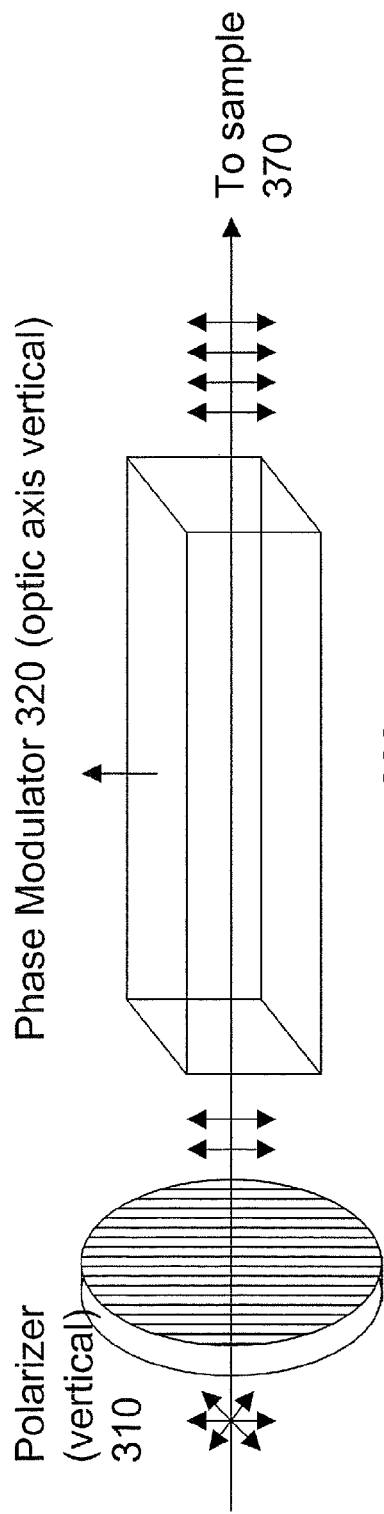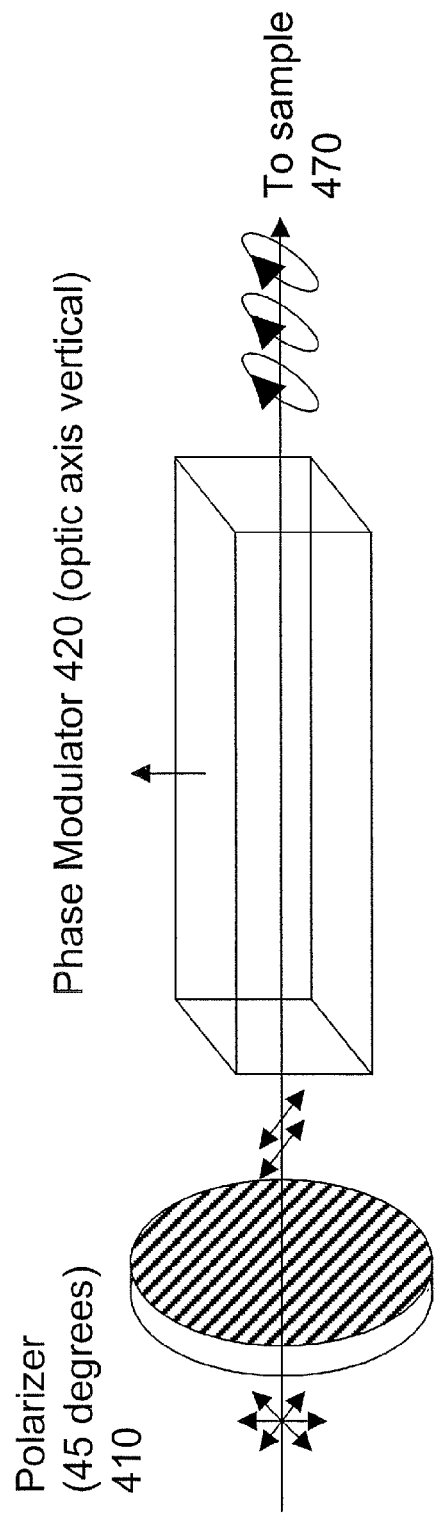

METHODS, SYSTEMS AND COMPUTER PROGRAM PRODUCTS FOR REMOVING UNDESIRED ARTIFACTS IN FOURIER DOMAIN OPTICAL COHERENCE TOMOGRAPHY (FDOCT) SYSTEMS USING CONTINUOUS PHASE MODULATION AND RELATED PHASE MODULATORS

CROSS-REFERENCE TO RELATED APPLICATION

The present application claims priority from U.S. Provisional Application No. 60/831,375, filed Jul. 17, 2006, the disclosure of which is hereby incorporated herein by reference as if set forth in its entirety.

FIELD OF THE INVENTION

The present invention relates to imaging and, more particularly, to optical coherence tomography (OCT) and related methods, systems and computer program products.

BACKGROUND OF THE INVENTION

Optical coherence tomography (OCT) is a noninvasive imaging technique that provides microscopic tomographic sectioning of biological samples. By measuring singly backscattered light as a function of depth, OCT fills a valuable niche in imaging of tissue ultrastructure, providing subsurface imaging with high spatial resolution (~2.0-10.0 µm) in three dimensions and high sensitivity (>10 dB) in vivo with no contact needed between the probe and the tissue.

In biological and biomedical imaging applications, OCT allows for micrometer-scale imaging non invasively in transparent, translucent, and/or highly-scattering biological tissues. The longitudinal ranging capability of OCT is generally based on low-coherence interferometry, in which light from a broadband source is split between illuminating the sample of interest and a reference path. The interference pattern of light reflected or backscattered from the sample and light from the reference delay contains information about the location and scattering amplitude of the scatterers in the sample. In time-domain OCT (TDOCT), this information is typically extracted by scanning the reference path delay and detecting the resulting interferogram pattern as a function of that delay. The envelope of the interferogram pattern thus detected represents a map of the reflectivity of the sample versus depth, generally called an A-scan, with depth resolution given by the coherence length of the source. In OCT systems, multiple A-scans are typically acquired while the sample beam is scanned laterally across the tissue surface, building up a two-dimensional map of reflectivity versus depth and lateral extent typically called a B-scan. The lateral resolution of the B-scan is approximated by the confocal resolving power of the sample arm optical system, which is usually given by the size of the focused optical spot in the tissue.

The time-domain approach used in conventional OCT, including commercial instruments, such as Carl Zeiss Meditec's StratusOCT® and Visante® products, has been successful in supporting biological and medical applications, and numerous in vivo human clinical trials of OCT reported to date have utilized this approach.

An alternate approach to data collection in OCT has been shown to have significant advantages both in reduced system complexity and in increased signal-to-noise ratio (SNR). This approach involves acquiring the interferometric signal generated by mixing sample light with reference light at a fixed group delay as a function of optical wavenumber. Two distinct methods have been developed which use this Fourier domain OCT (FD-OCT) approach. The first, generally termed Spectral-domain or spectrometer-based OCT (SDOCT), uses a broadband light source and achieves spectral discrimination with a dispersive spectrometer in the detector arm. The second, generally termed swept-source OCT (SSOCT) or optical frequency-domain imaging (OFDI), time-encodes wavenumber by rapidly tuning a narrowband source through a broad optical bandwidth. Both of these techniques may allow for a dramatic improvement in SNR of up to 15.0-20.0 dB over time-domain OCT, because they typically capture the A-scan data in parallel. This is in contrast to previous-generation time-domain OCT, where destructive interference is typically used to isolate the interferometric signal from only one depth at a time as the reference delay is scanned.

In both spectrometer-based and swept-source implementations of FDOCT, light returning from all depths is generally collected simultaneously, and is manifested as modulations in the detected spectrum. Transformation of the detected spectrum from wavelength to wavenumber, correction for dispersion mismatches between the sample and reference arms, and Fast Fourier transformation typically provides the spatial domain signal or "A-scan" representing depth-resolved reflectivity of the sample. The uncorrected A-scan may also include a strong DC component at zero pathlength offset, so-called "autocorrelation" artifacts resulting from mutual interference between internal sample reflections, as well as both positive and negative frequency components of the depth-dependent cosine frequency interference terms. Because of this, FDOCT systems typically exhibit "complex conjugate artifact" due to the fact that the Fourier transform of a real signal, the detected spectral interferogram, is typically Hermitian symmetric, i.e., positive and negative spatial frequencies are not independent. As a consequence, sample reflections at a positive displacement, relative to the reference delay, typically cannot be distinguished from reflections at the same negative displacement, and appear as upside-down, overlapping images on top of genuine sample structure, which generally cannot be removed by image processing. To reduce the likelihood of the occurrence of this symmetry artifact, FDOCT imaging is commonly performed with the entire sample either above or below the reference position, generally limiting the technique to thin samples of 2.0-4.0 mm, and placing the region of maximum SNR, at zero spatial frequency, outside the imaged structure. Resolving this artifact could effectively double the imaging depth, as well as allow the operator to position the most critical region of the sample at the position of maximum SNR.

SUMMARY OF THE INVENTION

Some embodiments of the present invention provide methods, fourier domain optical coherence tomography (FDOCT) interferometers and computer program products for removing undesired artifacts in FDOCT systems using continuous phase modulation. A variable phase delay is introduced between a reference arm and a sample arm of an FDOCT interferometer using continuous phase modulation. Two or more spectral interferograms having different phase delay integration times are generated. The spectral interferograms are combined using signal processing to remove the undesired artifacts.

In further embodiments of the present invention, FDOCT may include spectral domain optical coherence tomography (SDOCT).

In still further embodiments of the present invention, the undesired artifacts may include DC, autocorrelation and/or complex conjugate artifacts.

In some embodiments of the present invention, the variable phase delay may be introduced in the reference arm or the sample arm of the interferometer. In certain embodiments of the present invention, the variable phase delay may be introduced with a piezoelectric transducer associated with a mirror. The variable phase delay may also be introduced with an electro-optic, acousto-optic or photoelastic modulator in the reference arm or the sample arm of the FDOCT interferometer.

In further embodiments of the present invention, the variable phase delay may be provided by a phase modulator coupled to a driver. The driver is configured to provide signal and power to the phase modulator. The driver may include a function generator coupled to the phase modulator, a switching amplifier coupled to the function generator and a power supply coupled to the switching amplifier.

In still further embodiments of the present invention, the function generator may be configured to provide a tunable sine wave frequency having a range from about 1.0 Hz to about 1.0 MHz and a resolution of at least about 0.004 Hz; a Continuous phase variation from about 0.0 to about 360 degrees and a degree resolution of at least about 0.09; and/or a peak to peak voltage amplitude of from about 0.0 to about 20.0 V and a resolution of at least about 20.0 mV. In certain embodiments of the present invention, the function generator may be configured to use a direct digital synthesis (DDS) integrated circuit.

In some embodiments of the present invention, the power supply may include a Class D switching amplifier, a small value resistor in series with the phase modulator and/or a low pass filter. In certain embodiments of the present invention, the power supply may include a half-bridge switching amplifier.

In further embodiments of the present invention, continuous phase modulation may be linear continuous phase modulation. Linear continuous phase modulation may include shifting a phase in the reference arm or the sample arm linearly over a round trip delay of $2\phi=2\pi$ radians; integrating a spectral interferometric signal over three out of four evenly spaced sequential continuous phase shifts of $2\phi=\pi/2$ radians to provide a complex spectral interferogram; and inverse transforming the complex interferogram to provide an A-scan free the undesired artifacts. In certain embodiments of the present invention, the integration may be performed over more or less than three sequential continuous phase shifts.

In still further embodiments of the present invention, continuous phase modulation may include sinusoidal continuous phase modulation. Sinusoidal continuous phase modulation may include shifting a phase in one of the reference arm or the sample arm sinusoidally in a repetitive manner; integrating a spectral interferometric signal over four evenly spaced sequential quarter periods of the sinusoidal continuous phase modulation to provide a complex spectral interferogram; and inverse transforming the complex spectral interferogram to provide an A-scan free of undesired artifacts. In certain embodiments of the present invention, the integration may be performed over more or less than four quarter periods.

Some embodiments of the present invention provide systems that are switchable between stepped and continuous phase shifting Fourier domain optical coherence tomography (FDOCT) and polarization-sensitive optical coherence tomography (PSOCT) and associated methods. A phase/polarization modulator is configured to operate as a phase shifting modulator for artifact reduction in a first mode of operation and as a polarization modulator in a second mode of operation for polarization-sensitive optical coherence tomography (PSOCT).

In further embodiments of the present invention FDOCT may include Spectral domain optical coherence tomography (SDOCT).

In still further embodiments of the present invention, a linear polarizer may be coupled to the phase/polarization modulator. A transmissive direction of the linear polarizer may be in the same direction as an optic axis of the phase/polarization modulator during the first mode of operation. The linear polarizer may be rotated by 45 degrees in the second mode of operation.

In some embodiments of the present invention, the linear polarizer can be used for stepped or continuous phase modulation during the first mode of operation and the linear polarizer can be used for PSOCT in the second mode of operation.

In further embodiments of the present invention, the phase/polarization modulator may include an electro-optic phase modulator.

In still further embodiments of the present invention, a voltage applied to the electro-optic modulator may be increased during the first mode of operation, which increases a phase delay of polarized light passing through the electro-optic modulator. Furthermore, increasing the voltage applied to the electro-optic modulator during the second mode of operation may result in changing a polarization state of light exiting the modulator.

BRIEF DESCRIPTION OF THE DRAWINGS

FIG. 3 is a schematic block diagram illustrating a sample arm modulator in phase modulator position according to some embodiments of the present invention.

FIG. 4 is a schematic block diagram illustrating a sample arm modulator in polarization modulator position according to further embodiments of the present invention.

DETAILED DESCRIPTION OF EMBODIMENTS OF THE INVENTION

Figure 1:
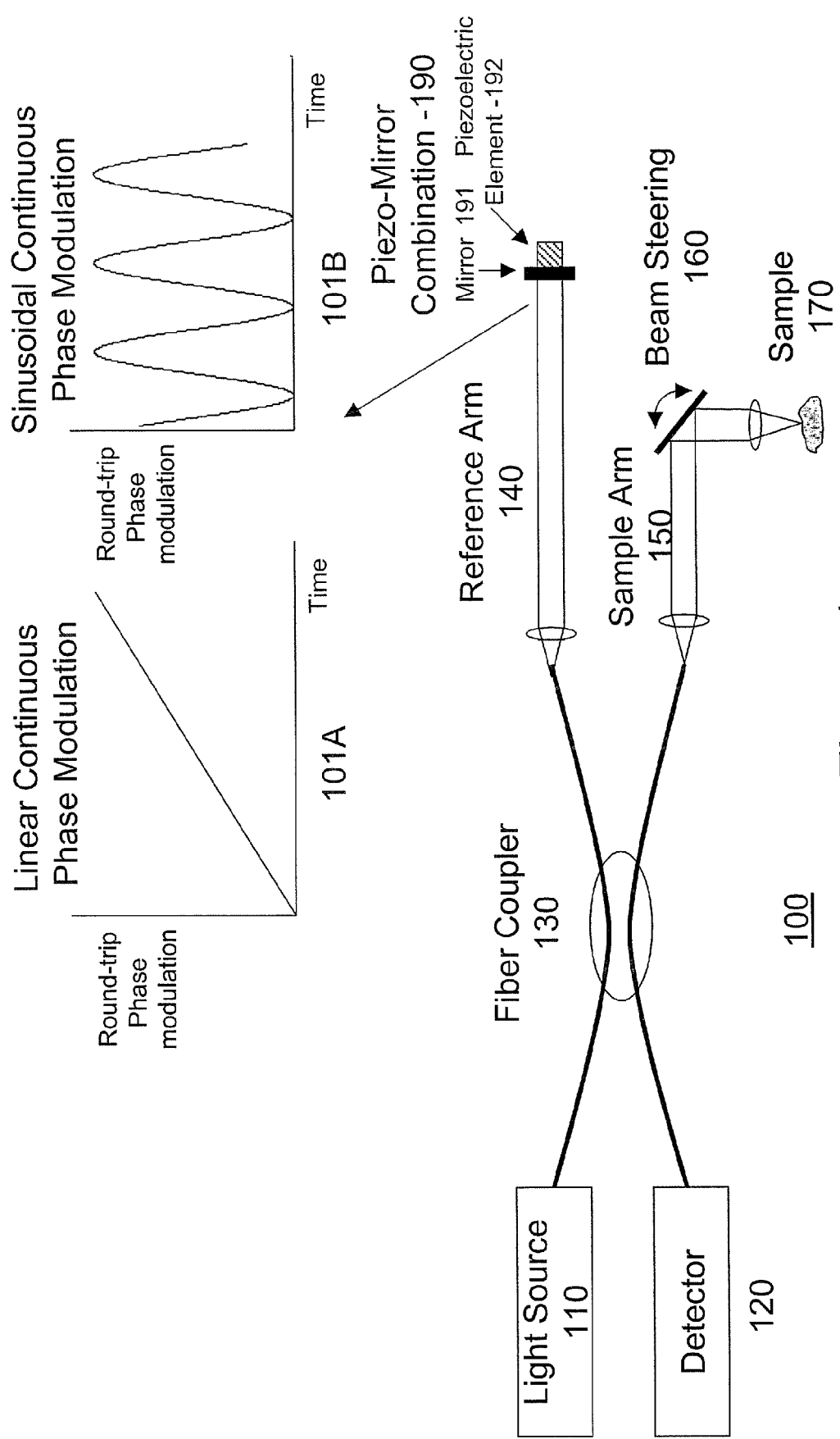
FIG. 1 is a schematic block diagram illustrating an optical coherence tomography (OCT) system including a piezoelectric transducer (PZT) element in accordance with some embodiments of the present invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

As will be appreciated by one of skill in the art, the invention may be embodied as a method, system, or computer program product. Accordingly, the present invention may take the form of an entirely hardware embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to a flowchart illustration and/or block diagrams of methods, systems and computer program products according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

It will be understood that, although the terms first, second, third etc. may be used herein to describe various elements, these elements should not be limited by these terms. These terms are only used to distinguish one element from another element. Thus, a first element discussed below could be termed a second element without departing from the scope of the present invention.

As will be discussed below with respect to FIGS. 1 through 7, undesired artifacts, such as the DC, autocorrelation, and complex conjugate artifacts in FDOCT, may be removed by utilizing principles and techniques borrowed from phase-shift interferometry. Several implementations of such "complex" FDOCT systems, and specifically spectral-domain or spectrometer-based OCT (SDOCT) systems, have been described which exploit stepped phase-shifting interferometry techniques to dither the phase of the reference or equivalently electric field using some sort of phase modulator, for example, a PZT mounted mirror or an arrangement of electro-optic, acousto-optic or photoelastic phase modulators, in one of the reference or sample arms of an SDOCT interferometer. Methods to obtain the complex signal using between two and five or even more discrete phase steps have been described.

Several methods also exist for extracting the polarization properties of samples, both depth-resolved birefringence and optical axis samples, using an extension of optical coherence tomography known as polarization-sensitive optical coherence tomography (PSOCT). Most methods previously described for PSOCT utilize some form of polarization elements or modulation in the source arm of the interferometer, utilize polarization-preserving fiber or count on non-polarization-preserving fiber to maintain the polarization state of the propagating wave in the absence of fiber motion, and utilize at least two receivers to concurrently monitor orthogonal polarization states of the interference optical signal. Fourier-domain versions of PSOCT systems have also been described, however the requirement to support two simultaneous detection channels may be particularly burdensome in the spectrometer-based SDOCT version of FDOCT, which may require expensive and sensitive spectrometers and array detectors in each detector channel. One previously disclosed method for PSOCT, as discussed in *Simplified method for polarization-sensitive optical coherence tomography* by Roth et al. (Optic letters, Vol. 26, No. 14, July 2001), was implemented generally as a modification of a TDOCT system. This PSOCT design generally involved placement of a polarization modulator in the sample arm of the interferometer with no other hardware modifications from a standard TDOCT system. The polarization modulator included a linear polarizer followed by an addressable wave plate (AWP) with its optical axis oriented at 45° to the polarizer transmission axis. These two components acted in combination as a polarization modulator capable of placing light with desired polarization states on the sample. Previously, a signal processing algorithm was described which involved using the polarization modulator to place three or more polarization states sequentially on the sample. A signal processing algorithm was described which calculated the depth-resolved birefringence and optical axis of the sample from the set of three or more OCT signal amplitudes detected with the modulator thusly used.

Thus, some embodiments of the present invention provide methods, systems and computer program products for removing undesired artifacts, such as the DC, autocorrelation, and complex conjugate artifacts, in FDOCT systems using continuous rather than discrete phase shifting. Further embodiments of the present invention provide methods, systems and computer program products designed for either stepped or continuous phase shifting FDOCT, which are switchable between phase shifting for artifact reduction and polarization modulation for PSOCT applications as will be discussed further below.

Referring to FIG. 1, a schematic block diagram illustrating an optical coherence tomography (OCT) system 100 including a piezoelectric transducer (PZT) element in accordance with some embodiments of the present invention will be discussed. As illustrated in FIG. 1, the system 100 includes a light source 110, a detector 120, a fiber coupler 130, a reference delay 140, a piezo-mirror combination 190, a beam steering unit 160, a sample arm 150 and a sample 170. In some embodiments of the present invention, the light source 110 includes a broadband light source and the detector 120 includes a spectrometer illuminating a multichannel detector, such as a linear charge-coupled device (CCD) array. A piezo-mirror combination 190 is located in the reference arm 140 of the interferometer, which may include a mirror 191 and a piezoelectric element 192 as illustrated therein.

Thus, embodiments of the present invention illustrated in FIG. 1 replace a phase modulator with a piezo-mirror combination 190 implemented as a mirror 191 mounted on a PZT element 192 at the termination of the reference arm 140. Systems including the piezo-mirror combination 190 will be discussed further below with respect to FIG. 7. As further illustrated conceptually by the graphs in FIG. 1, the piezo-mirror combination 190 can be used to implement linear continuous phase modulation by, for example, having the PZT element 192 continuously scan the mirror 191 in one direction 101A or linear sinusoidal phase modulation by, for example, having the PZT element 192 continuously scan the mirror back and forth in a sinusoidal pattern 101B.

It will be understood that although the piezo-mirror combination 190 is provided in the reference arm 140 of FIG. 1, embodiments of the present invention are not limited to this configuration. For example, the piezo-mirror combination 190 may be provided in the sample arm 150 without departing from the scope of the present invention.

Figure 2:
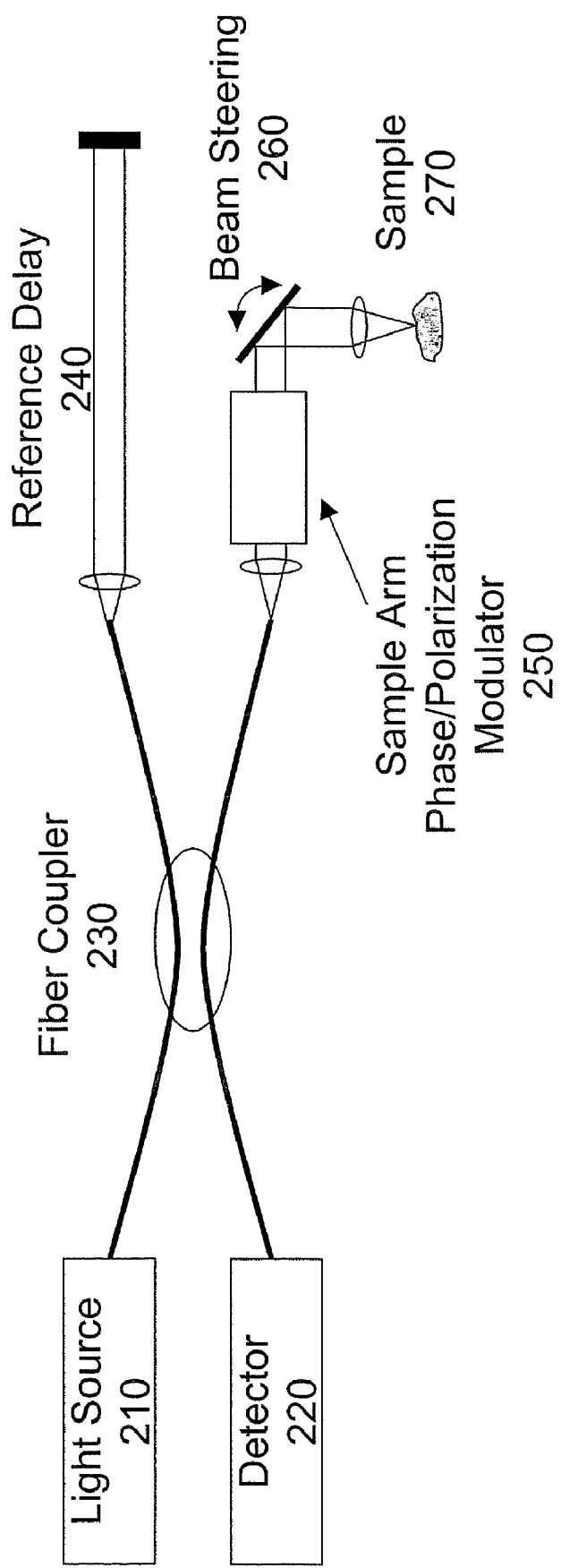
FIG. 2 is a schematic block diagram illustrating a fiber optic Spectral-domain or spectrometer-based OCT (SDOCT) system including a phase/polarization modulator in the sample arm which provides for continuous phase modulation complex conjugate resolved imaging, and is also switchable between complex conjugate resolved imaging and polarization-sensitive optical coherence tomography (PSOCT) imaging according to some embodiments of the present invention

Referring now to FIG. 2, a fiber optic SDOCT system 200 including a phase/polarization modulator in the sample arm will be discussed. As illustrated in FIG. 2, the system 200 includes a light source 210, a detector 220, a fiber coupler 230, a reference delay 240, a sample arm phase/polarization modulator 250, a beam steering unit 260 and a sample 270. The light source 210 includes a broadband light source and the detector 220 includes a spectrometer illuminating a multichannel detector, such as a linear charge-coupled device (CCD) array. A phase/polarization modulator 250 is located in the sample arm of the interferometer, which may include a linear polarizer followed by an addressable wave plate (AWP) with its optical axis oriented at 45° to the polarizer transmission axis, discussed further below. The phase/polarization modulator 250 may be switchable between first and second modes in accordance with some embodiments of the present invention. For example, the phase/polarization modulator 250 may act as a phase modulator in a first mode and a polarization modulator in a second mode capable of placing light with desired phase delay or polarization states on the sample 270.

Some embodiments of the present invention provide a specific hardware system for implementation of either stepped or continuous phase-shifting FDOCT, which is readily switchable between phase shifting for artifact reduction and polarization modulation for PSOCT applications. This system, for example, modulator 250, may be placed in the optical path of the FDOCT system between the sample arm fiber and the sample 270 as illustrated in FIG. 2. Hardware implementations of modulators with two alternate configurations according to some embodiments of the present invention are illustrated in FIGS. 3 and 4.

FIG. 3 is a schematic block diagram illustrating a sample arm modulator in phase shifting modulator position (first mode) according to some embodiments of the present invention. FIG. 4 is a schematic block diagram illustrating a sample arm modulator in polarization modulator position (second mode) according to some embodiments of the present invention.

Referring now to FIGS. 3 and 4, both systems 300 and 400 include a linear polarizer 310 and 410, which may be absorptive, or implemented using optical coatings, followed by an electro-optic phase modulator 320 and 420. When the transmissive direction of the polarizer 310 is in the same direction, i.e., vertical, as the optic axis of the phase modulator 320 (as illustrated in FIG. 3), the modulator 320 is in the phase modulator configuration and can be used for stepped or continuous-phase modulation as described. In this orientation, increasing the voltage applied to the electro-optic modulator may result in increasing the phase delay of the polarized light passing through the modulator, as needed for stepped or continuous-phase modulation methods as described. Furthermore, either the polarizer or the phase modulator may be rotated by 45° to place the modulator in the polarization modulator configuration as illustrated in FIG. 4. In this polarization modulator configuration, the modulator may be used to perform polarization-sensitive OCT as discussed. In this orientation, increasing the voltage applied to the electro-optic modulator results in changing the polarization state of the light exiting the modulator, as needed for PSOCT methods According to some embodiments of the present invention, the spectral data acquired for each polarization configuration may be converted to depth-dependent reflectivity data prior to inclusion in the PSOCT methods for calculation of depth-dependent birefringence and optic axis orientation of the sample.

Some embodiments of the present invention provide methods for removing undesired artifacts in Fourier domain optical coherence tomography (FDOCT) systems using continuous phase modulation. According to some embodiments of the present invention, a method for continuous phase-shift interferometry is particularly desirable for FDOCT systems optimized for high speed imaging. Most conventional phase estimation methods typically assume that the spectral interferogram is sampled for discrete sequential or simultaneous values of the phase shift. However, realization of this situation in practice can be difficult if rapid acquisition is desired, because phase-shift devices that depend upon mechanical motions (such as piezoelectric or photoelastic elements) electro-optic devices (such as phase modulators), and acousto-optic devices (such as differential achromatic acousto-optic modulation), typically tend to oscillate sinusoidally. Attempting to sample the spectral interferometric signal from these devices only at specific phase shifts, as has been done so far in FDOCT, may be wasteful of signal power, which is valuable in OCT. Methods are described herein for using both linear and sinusoidal phase modulation for artifact removal in FDOCT. These methods are referred to herein as "integrating bucket" methods, because they have typically been designed for charge integrating detectors, such as charge-coupled devices, and they generally operate by integrating the charge acquired over a portion, typically $\pi/2$, of the cyclical phase modulation.

As discussed herein, according to some embodiments of the present invention, the undesired artifacts, such as DC, autocorrelation, and complex conjugate artifacts in FDOCT may be removed introducing a variable single-pass phase delay $\phi$ (round-trip phase delay $2\phi$) between the reference and sample arms, acquiring a set of spectral interferograms with different phase delays which can be combined in signal processing to eliminate the undesired artifacts.

Figure 5:
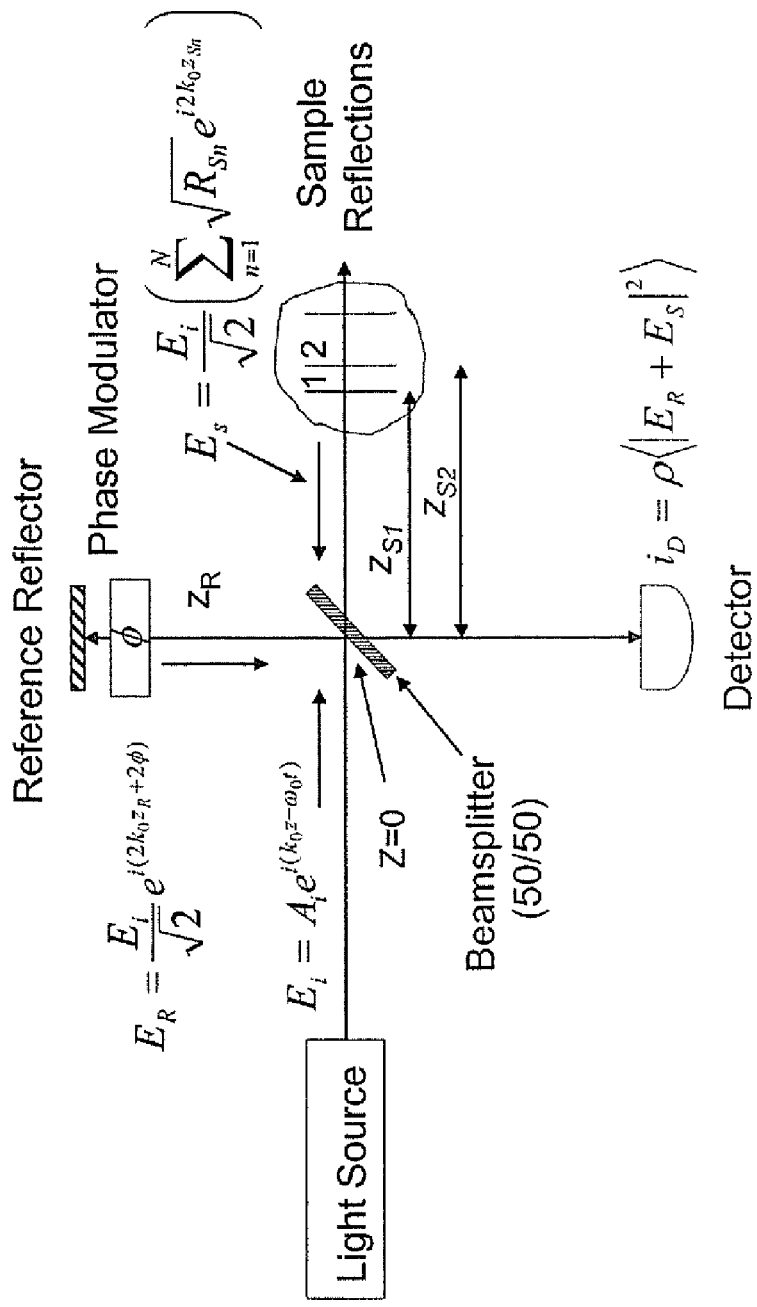
FIG. 5 is a schematic block diagram illustrating an interferometer used for continuous phase modulation according to some embodiments of the present invention.

In particular, an FDOCT interferometer 500 with a variable phase modulator placed in the reference arm is provided in FIG. 5. Details will be discussed with respect to embodiments having the variable phase modulator in the reference arm, however embodiments of the present invention are not limited to this configuration. As illustrated in FIG. 5, the reference field returning from the reference arm is modified to $$E_R = \frac{E_i}{\sqrt{2}} e^{i(2kz_R + 2\phi)}.$$

There are a number of approaches for introducing such phase delays. Phase modulators based on electro-optic, acousto-optic, and photoelastic modulators may be utilized, or the reference mirror itself may be dithered by mounting it on a mechanical transducer, such as a PZT. A piezoelectric system will be discussed below with respect to FIG. 7. Such transducers have the advantage of relative simplicity, though their use requires that phase-shifted spectral interferograms be acquired sequentially; the resulting artifact reduction occurs at the cost of increased acquisition time.

Phase-shifted spectral interferograms may also be acquired simultaneously on separate detectors by employing interferometer topologies which intrinsically separate phase-shifted signals into different detector channels. Such simultaneous phase-shifted interferometers have been constructed which use orthogonal polarization states to carry phase-shifted signals, or which employ 3×3 or higher order fiber couplers to separate phase channels.

An equation for the photocurrent detected in each spectral channel of a FDOCT system with the additional phase delay explicitly included yields Equation (1):

$$I_D(k, 2\phi) = \rho\left[\frac{S(k)}{2}[1 + R_{S1} + R_{S2} + \dots ]\right] \text{"DC Terms"} +$$

$$\rho\left[S(k)\sum_{n=1}^{N} r_{Sn}(\cos[2k(z_R - z_{Sn})] + 2\phi)]\right] \text{"Cross-correlation Terms"} +$$

-continued $$\rho\left[\frac{S(k)}{2}\sum_{n\neq m=1}^{N} r_{Sn}r_{Sm}\cos[2k(z_{Sn} - z_{Sm})]\right] \text{"Auto-correlationTerms"}$$

In this equation, k represents the wavenumber of light, $\rho$ represents the responsivity of the detector, S(k) represents the power spectrum of the light source, $z_R$ represents the length of the reference arm of the interferometer, and there are assumed to be N reflectors having amplitude reflectivity $r_{Sn}$ and power reflectivity $R_{Sn}$ located at length positions $z_{Sn}$ in the sample arm of the interferometer.

Since typically most, but not all, types of phase modulators generate slightly different phase delays as a function of optical wavelength or wavenumber, it will be understood that the specific phase delays referred to in the following should be understood as referring to the approximate central wavelength of the light source. Small errors in complex conjugate artifact removal due to the chromaticity of the phase delays may simply be tolerated, or may be ameliorated by additional signal processing steps such as discussed in M. V. Sarunic, B. E. Applegate, and J. A. Izatt, *Real Time Quadrature Projection Complex Conjugate Resolved Fourier Domain Optical Coherence Tomography* (Optics Letters 31:2426-2428, 2006), the disclosure of which is hereby incorporated herein by reference as if set forth in its entirety.

If a spectral interferogram with round-trip phase delay $2\phi=\pi$ is acquired and subtracted from a spectral interferogram acquired with no phase delay, then it follows from Equation (1) that the DC and autocorrelation terms will be eliminated and the cross-correlation terms doubled as illustrated by Equation (2):

$$I_D(k, 2\phi = 0) - I_D(k, 2\phi = \pi) = 2\rho\left[S(k)\sum_{n=1}^{N} r_{Sn}(\cos[2k(z_R - z_{Sn})])\right].$$

The reversal of the sign of the cosine which gives rise to this result clearly depends only upon the $2\phi=\pi$ phase difference between the spectral interferograms and not upon any arbitrary phase offset to both of them, thus it is important for this and all of the following results in this section that the phase-shifted interferograms be acquired either simultaneously, or else quickly compared to any substantial phase drifting time in the interferometer. The A-scan which results from the inverse Fourier transform of Equation (2) also contains only cross-correlation terms, thus the DC and autocorrelation artifacts (but not the complex conjugate artifact) may be eliminated using this 2-step algorithm (Equation (3)):

$$i_D(z, 2\phi = 0) - i_D(z, 2\phi = \pi) = \rho\sum_{n=1}^{N} r_{Sn}[\gamma[2(z_R - z_{Sn})] + \gamma[-2(z_R - z_{Sn})]].$$

In this equation, $\gamma(z)$ represents the autocorrelation function of the light source of the interferometer.

To remove the complex conjugate artifact, at least two spectral interferograms with non-complementary phase delays (i.e., with $2\phi$ different than $\pi$ radians) are acquired. For example, if a spectral interferogram with round-trip phase delay $2\phi=3\pi/2$ is subtracted from a spectral interferogram acquired with round-trip phase delay $2\phi=\pi/2$, the result is a spectral interferogram containing only cross-correlation terms which is in phase quadrature with the previous result (Equation (4)):

$$I_D(k, 2\phi = 3\pi/2) - I_D(k, 2\phi = \pi/2) = 2\rho\left[S(k)\sum_{n=1}^{N} r_{Sn}(-\sin[2k(z_R - z_{Sn})])\right].$$

Combining all four phase-shifted interferograms yields the result (Equation (5)):

$$I_D(k, 2\phi = 0) - I_D(k, 2\phi = \pi) + j[I_D(k, 2\phi = \pi/2) - I_D(k, 2\phi = 3\pi/2)] =$$
$$2\rho\left[S(k)\sum_{n=1}^{N} r_{Sn}(\cos[2k(z_R - z_{Sn})] - j\sin[2k(z_R - z_{Sn})])\right].$$

This 4-step combination of phase-shifted spectral interferograms inverse transforms to an A-scan free of DC, autocorrelation and complex conjugate artifacts, which is the desired result (Equation (6)):

$$i_D(z, 2\phi = 0) - i_D(z, 2\phi = \pi) + j[i_D(z, 2\phi = \pi/2) - i_D(z, 2\phi = 3\pi/2)] =$$
$$\rho\sum_{n=1}^{N} r_{Sn}[\gamma[2(z_R - z_{Sn})] + \gamma[-2(z_R - z_{Sn})] + \gamma[2(z_R - z_{Sn})] -$$
$$\gamma[-2(z_R - z_{Sn})]] = 2\rho\sum_{n=1}^{N} r_{Sn}\gamma[2(z_R - z_{Sn})]$$

It should be noted that if the DC and autocorrelation artifacts are removed through some independent means, i.e. by subtracting averaged spectral interferogram data from each individual spectral interferogram, then only two phase steps separated by $2\phi = \pi/2$ are required, i.e. (Equation (7))

$$i_D(z, 2\phi = 0) + j[i_D(z, 2\phi = \pi/2)] = 2\rho\sum_{n=1}^{N} r_{Sn}\gamma[2(z_R - z_{Sn})]$$

is also true if the component A-scans contain only cross-correlation terms.

The problem of artifact removal can equivalently be stated as the problem of uniquely identifying the amplitude and phase of the cross-correlation cosine. Thus, the large assortment of algorithms which have been developed for phase-shift interferometry, including those which utilize three, five, or more phase shifts in optimal combinations to increase accuracy, may readily be applied to FDOCT.

One set of algorithms from phase-shift interferometry which are particularly germaine to FDOCT systems optimized for high speed are those which use continuous rather than discrete phase shifting. Some embodiments of the present invention use linear continuous phase modulation. In these embodiments of the present invention, the algorithm assumes that the phase is shifted linearly over $2\phi = 2\pi$ in a sawtooth-like manner, and that the spectral interferometric signal is integrated over three out of four evenly spaced sequential buckets. Applying this approach to integrate the spectral interferometric signal Equation (1) over three sequential continuous phase shifts of $2\phi = \pi/2$ results in Equation (8).

$$\int_0^{\pi/2} I_D(k, 2\phi)d(2\phi) =$$
$$DC + Autocorr + \rho\left[S(k)\sum_{n=1}^{N} r_{Sn}(\cos[2k(z_R - z_{Sn})] - \sin[2k(z_R - z_{Sn})])\right]$$
$$\int_{\pi/2}^{\pi} I_D(k, 2\phi)d(2\phi) = DC + Autocorr +$$
$$\rho\left[S(k)\sum_{n=1}^{N} r_{Sn}(-\cos[2k(z_R - z_{Sn})] - \sin[2k(z_R - z_{Sn})])\right]$$
$$\int_{\pi}^{3\pi/2} I_D(k, 2\phi)d(2\phi) = DC + Autocorr +$$
$$\rho\left[S(k)\sum_{n=1}^{N} r_{Sn}(-\cos[2k(z_R - z_{Sn})] - \sin[2k(z_R - z_{Sn})])\right]$$

As was the case for discrete phase shifting, combining the integrated buckets results in a complex spectral interferogram Equation (9):

$$\int_0^{\pi/2} I_D(k, 2\phi)d(2\phi) - \int_{\pi/2}^{\pi} I_D(k, 2\phi)d(2\phi) +$$
$$j\left[\int_{\pi}^{3\pi/2} I_D(k, 2\phi)d(2\phi) - \int_{\pi/2}^{\pi} I_D(k, 2\phi)d(2\phi)\right] =$$
$$2\rho\left[S(k)\sum_{n=1}^{N} r_{Sn}(\cos[2k(z_R - z_{Sn})] - j\sin[2k(z_R - z_{Sn})])\right].$$

This 3-step combination of integrated-bucket spectral interferograms inverse transforms to an A-scan free of DC, autocorrelation and complex conjugate artifacts, which is the desired result (Equation (10)):

$$I.F.T\left[\int_0^{\pi/2} I_D(k, 2\phi)d(2\phi) - \int_{\pi/2}^{\pi} I_D(k, 2\phi)d(2\phi) +$$
$$j\left[\int_{\pi}^{3\pi/2} I_D(k, 2\phi)d(2\phi) - \int_{\pi/2}^{\pi} I_D(k, 2\phi)d(2\phi)\right]\right] =$$
$$2\rho\sum_{n=1}^{N} r_{Sn}\gamma[2(z_R - z_{Sn})]$$

Some embodiments of the present invention use sinusoidal continuous phase modulation. In these embodiments of the present invention, it is assumed that the phase is shifted sinusoidally in an oscillatory manner, such as might be achieved for example by a piezo-electric modulator oscillating back and forth, or a photoelastic modulator. In this embodiment, the spectral interferometric signal becomes an explicit function of time_t (Equation (11)):

$$I_D(k, 2\psi, f, \theta, t) = \rho\left[\frac{S(k)}{2}[1 + R_{S1} + R_{S2} + \dots]\right] \text{ "DC Terms"} +$$

-continued $$\rho\left[S(k)\sum_{n=1}^{N}r_{Sn}(\cos[2k(z_R-z_{Sn})]+2\psi\sin(2\pi ft+\theta)])\right]$$

"Cross-correlation Terms" +

$$\rho\left[\frac{S(k)}{2}\sum_{n\ne m=1}^{N}r_{Sn}r_{Sm}\cos[2k(z_{Sn}-z_{Sm})]\right]\text{"Auto-}correlationTerms\text{"}$$

Here it is assumed that the round-trip phase is modulated in a sinusoidal manner with period T=1/f, amplitude 2ψ, and phase θ. One algorithm for sinusoidal continuous phase-shift integrating-bucket interferometry consists of integrating the spectral interferometric signal over four sequential quarters of the modulation period T (Equation (12)):

Linear combinations of the four integrations can then be formed as (Equation (13)):

$$-E_1+E_2+E_3-E_4=(4T/\pi)\Gamma_s\rho\left[S(k)\sum_{n=1}^{N}r_{Sn}(\sin[2k(z_R-z_{Sn})])\right],$$

$$-E_1+E_2-E_3+E_4=(4T/\pi)\Gamma_c\rho\left[S(k)\sum_{n=1}^{N}r_{Sn}(\cos[2k(z_R-z_{Sn})])\right].$$

For optimal values of the modulation amplitude 2ψ=2.45 and phase θ=0.96, then $\Gamma_s=\Gamma_c=\Gamma=0.405$. Thus, these 4-step combinations of integrated-bucket spectral interferograms may be combined as follows in FDOCT to inverse transform spectral interferometric data to an A-scan free of DC, autocorrelation, and complex conjugate artifacts as well (Equation (14)):

$$I.F.T[(-E_1+E_2+E_3-E_4)-j(-E_1+E_2-E_3+E_4)]=$$

$$(4T/\pi)\Gamma\rho\sum_{n=1}^{N}r_{Sn}\gamma[2(z_R-z_{Sn})].$$

Figure 6:
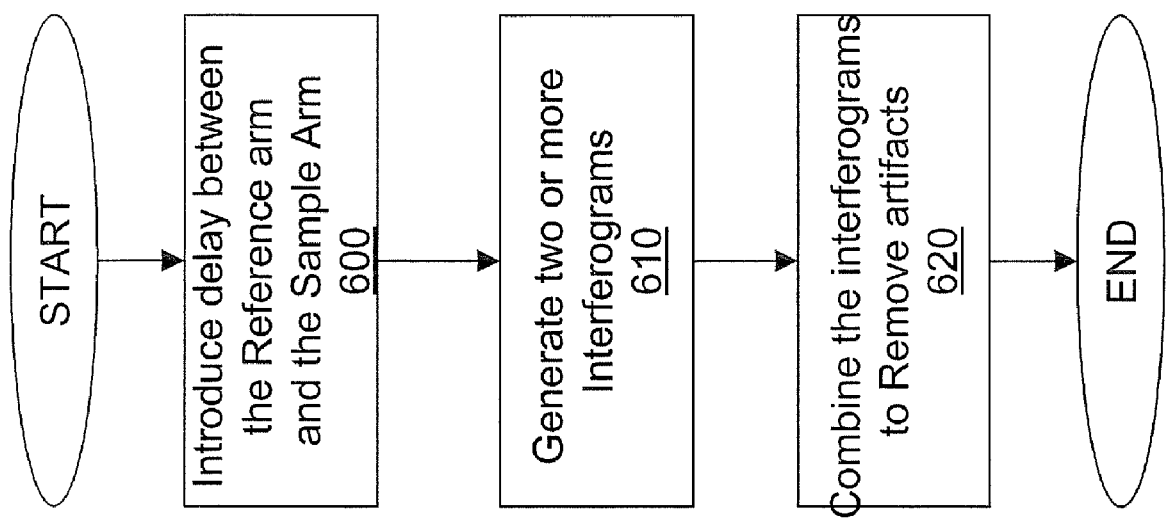
FIG. 6 is a flowchart illustrating operations of continuous phase modulation in accordance with some embodiments of the present invention.

Operations for continuous phase modulation will now be discussed with respect to the flowchart of FIG. 6. Operations begin at block 600 for methods for removing undesired artifacts in FDOCT systems using continuous phase modulation by introducing a variable phase delay between a reference arm and a sample arm of an FDOCT interferometer using continuous phase modulation. Two or more spectral interferograms are generated having different integration times (block 610). The spectral interferograms are combined using signal processing to remove the undesired artifacts (block 560).

In some embodiments of the present invention, the undesired artifacts include DC, autocorrelation and/or complex conjugate artifacts. The variable phase delay may be introduced in the reference arm or the sample arm of the interferometer. In some embodiments of the present invention, the delay may be introduced using a mirror mounted to a piezoelectric transducer or an electro-optic, acousto-optic or photoelastic modulator in the reference arm or the sample arm of the FDOCT interferometer.

Some embodiments of the present invention use linear continuous phase modulation. Linear continuous phase modulation includes shifting a phase in the reference arm or the sample arm linearly over a round trip delay of 2φ=2π radians. A spectral interferometric signal is integrated over three out of four evenly spaced sequential continuous phase shifts of 2φ=π/2 to provide a complex spectral interferogram. The complex interferogram is inverse transformed to provide an A-scan free the undesired artifacts. In certain embodiments of the present invention, the spectral interferometric signal may be integrated over more or less than three sequential continuous phase shifts.

Further embodiments of the present invention use sinusoidal continuous phase modulation. Sinusoidal continuous phase modulation may include shifting a phase in one of the reference arm or the sample arm sinusoidally in a repetitive manner. A spectral interferometric signal is integrated over four evenly spaced sequential quarter periods of the sinusoidal continuous phase modulation to provide a complex spectral interferogram. The complex spectral interferogram is inverse transformed to provide an A-scan free of undesired artifacts. In certain embodiments of the present invention, the spectral interferometric signal may be integrated over more or less than four quarter periods.

Figure 7:
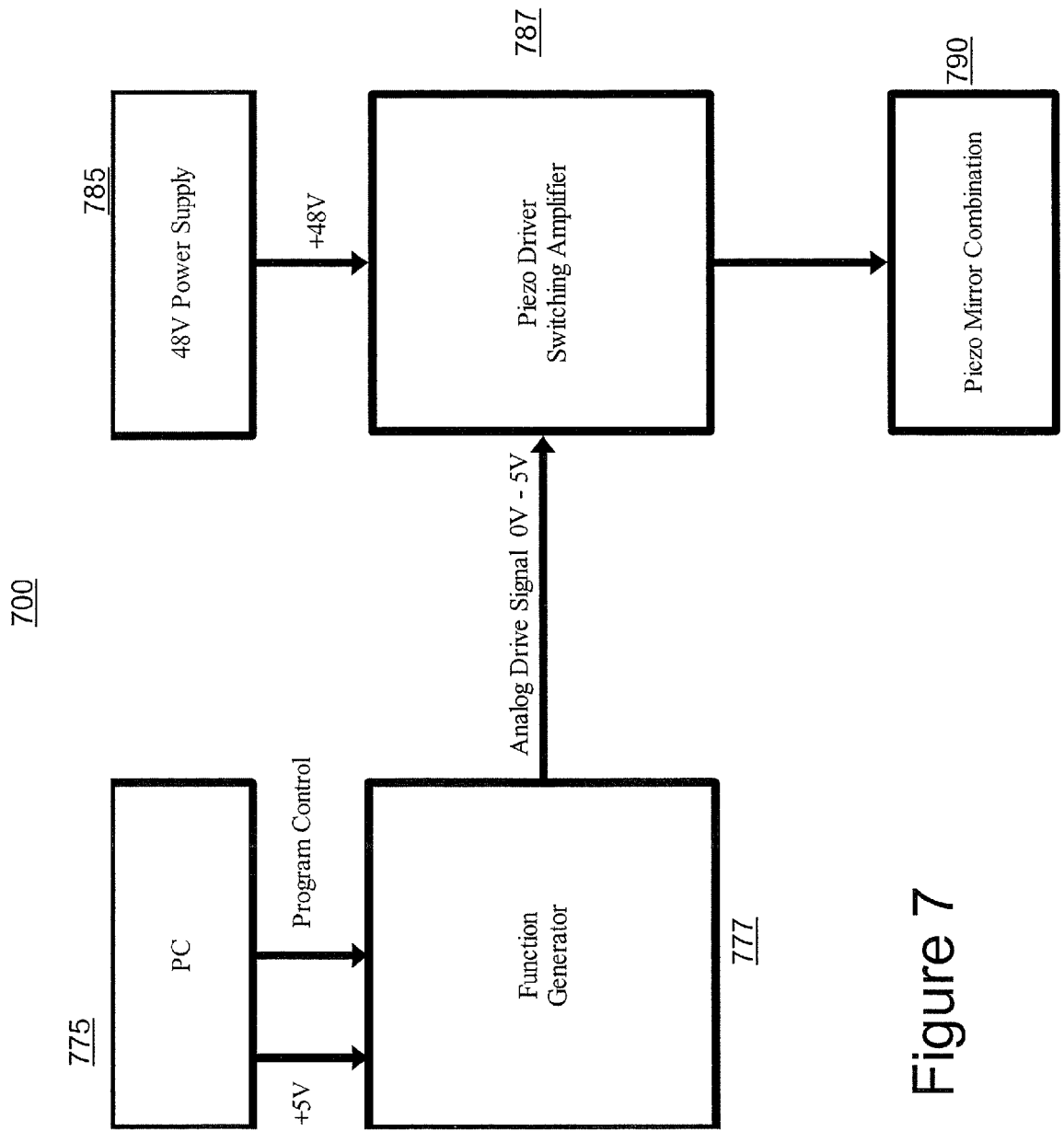
FIG. 7 is a system block diagram including a Piezo driver in accordance with some embodiments of the present invention.

Referring now to FIG. 7, a system including a piezo driver to actuate the piezo mirror combination illustrated in FIG. 1 according to some embodiments of the present invention will be discussed. As illustrated in FIG. 7, the system 700 includes a computer 775 or communications device, a function generator 777, a piezo driver switching amplifier 787, a power supply 785 and a piezo mirror combination 790. In some embodiments of the present invention, the power supply 785 may be a 48 V power supply.

The piezo driver 787 requirement is for a small and powerful drive system to drive the piezo actuator. The function generator 777 has the flexibility to vary the sine wave frequency over several thousand kHz, vary the phase from 0 to 360 degrees and vary the voltage output from 0 to 20 Vpp.

The piezo driver 787 is for a small powerful system and, therefore, is provided by a switching amplifier in accordance with some embodiments of the present invention. Most switching amplifiers, also referred to as Class D amplifiers, are used as audio amplifiers or as motor controllers. Driving a piezo actuator with a switching amplifier may be difficult primarily because the load is purely capacitive. Driving a capacitive reactive load is difficult to do with a switching amplifier because the control-loop will be difficult to stabilize. In some embodiments of the present invention, this potential problem may be addressed by placing a small value resistor in series with the piezo actuator. The resistor may have a value of about 0.47 ohms, which may allow enough gain and phase margin needed for a stable control-loop. Furthermore, the resistor is small, dissipating little power and can also function as an over-current sense resistor.

In some embodiments of the present invention, the amplifier 787 may use a small inductor in series with the piezo actuator that would form a low pass LC filter. This filter removes most of the high frequency switching noise (carrier) leaving only the low frequency drive voltage input from the function generator 777. The inductor may be, for example, about 10 uH toroid which removes over half the amplitude of the carrier frequency. Removing the entire carrier is not necessary since the piezo actuator is not able to react to the 500 kHz amplifier switching frequency.

Finally, the piezo amplifier is for a DC bias of half the supply voltage. Whatever the supply voltage is, driving it with a DC bias of Vsupply/2 will allow the AC signal to ride on top of the DC level and swing from Vsupply/2 to Vsupply or from Vsupply/2 to 0V. This method allows for the least amount of stress on the piezo actuator. For this reason a half-bridge switching amplifier may be selected, because it inherently achieves this requirement.

As discussed above, in some embodiments of the present invention, the driver operates from a +48V supply 785 switching at 500 kHz, with a DC bias of 24V across the actuator. In some embodiments of the present invention, the bus voltage may be from about +24V to about +36V.

The function generator 777 may use a direct digital synthesis (DDS) integrated circuit. The DDS chip enables frequency and phase variation. The voltage variation may be implemented using an operational amplifier (op-amp) to increase the fixed output voltage of the DDS chip. After the voltage is maximized by the op-amp it may be routed to a programmable resistor integrated circuit to vary its amplitude. Both the DDS chip and the programmable resistor chip are programmed with several digital lines. The function generator 777 may also be synchronized with the camera scan rate. In some embodiments of the present invention, this may be accomplished by resetting the DDS chip with external logic and a sync signal coming from the PC.

The foregoing is illustrative of implementations using Fourier domain OCT architectures, with emphasis on Spectral domain architectures, Those skilled in the art will recognize that the primary difference among FDOCT implementations, for example, between Swept-Source (SS) and Spectral Domain (SD) implementations, is that in SD implementations each complete phase-specific spectral interferogram is acquired in parallel, whereas in SS implementations, the spectral interferogram is acquired in a serial acquisition as the spectrum is tuned rapidly over the wavelength band.

This serial spectral acquisition suggests an alternative strategy to the phase modulation approach to "complex" Swept Source OCT and the associated techniques as described herein. Specifically, for each pass of the tuned spectrum, an associated phase ramp may be applied. A deterministic, but wavelength-variant, phase is imposed on the acquired spectral interferogram. A plurality of sequential serial spectral interferograms may be then acquired with appropriate offsets to the initial condition of the applied phase ramp. The signal processing to recover and apply the amplitude and phase of the spectral interferogram for complex conjugate reconstruction or PSOCT may then follow the general prescriptions for FDOCT in general, and SDOCT specifically, accounting for the wavelength-variant phases.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for removing undesired artifacts in Fourier domain optical coherence tomography (FDOCT) systems using continuous phase modulation, comprising:

introducing a variable phase delay between a reference arm and a sample arm of an FDOCT interferometer using continuous phase modulation;

generating two or more spectral interferograms having different phase delay integration times; and combining the spectral interferograms using signal processing to remove the undesired artifacts.

2. The method of claim 1, wherein FDOCT comprises Spectral domain optical coherence tomography (SDOCT).

3. The method of claim 2, wherein the undesired artifacts comprise DC, autocorrelation and/or complex conjugate artifacts.

4. The method of claim 2, wherein introducing the variable phase delay comprises including the variable phase delay in the reference arm or the sample arm of the interferometer.

5. The method of claim 2, wherein introducing the variable phase delay comprises introducing the variable phase delay using a piezoelectric transducer associated with a mirror.

6. The method of claim 2, wherein introducing the variable phase delay comprises introducing the variable phase delay using an electro-optic, acousto-optic or photoelastic modulator in the reference arm or the sample arm of the FDOCT interferometer.

7. The method of claim 2, wherein continuous phase modulation comprises linear continuous phase modulation.

8. The method of claim 7, wherein linear continuous phase modulation comprises:

shifting a phase in the reference arm or the sample arm linearly over a round trip delay of $2\phi=2\pi$ radians;

integrating a spectral interferometric signal over three out of four evenly spaced sequential continuous phase shifts of $2\phi=\pi/2$ radians to provide a complex spectral interferogram; and inverse transforming the complex interferogram to provide an A-scan free the undesired artifacts.

9. The method of claim 8, wherein integrating further comprises integrating over more than three sequential continuous phase shifts.

10. The method of claim 8, wherein integrating further comprises integrating over less than three sequential continuous phase shifts.

11. The method of claim 2, wherein continuous phase modulation comprises sinusoidal continuous phase modulation.

12. The method of claim 11, wherein sinusoidal continuous phase modulation comprises:

shifting a phase in one of the reference arm or the sample arm sinusoidally in a repetitive manner;

integrating a spectral interferometric signal over four evenly spaced sequential quarter periods of the sinusoidal continuous phase modulation to provide a complex spectral interferogram; and inverse transforming the complex spectral interferogram to provide an A-scan free of undesired artifacts.

13. The method of claim 12, wherein integrating further comprises integrating over more than four quarter periods.

14. The method of claim 12, wherein integrating further comprises integrating over less than four quarter periods.

15. A Fourier domain optical coherence tomography (FDOCT) interferometer comprising a variable phase modulator configured to introduce a variable phase delay between a reference arm and a sample arm of the FDOCT interferometer using continuous phase modulation, wherein the FDOCT interferometer comprises a Spectral domain optical coherence tomography (SDOCT) interferometer, the SDOCT interferometer being further configured to:

introduce a variable phase delay between a reference arm and a sample arm of the SDOCT interferometer using linear continuous phase modulation, shift a phase in the reference arm or the sample arm linearly over a round trip delay of $2\phi=2\pi$ radians;

integrate a spectral interferometric signal out of four evenly spaced sequential continuous phase shifts of $2\phi=\pi/2$ radians to provide a complex spectral interferogram; and inverse transform the complex interferogram to provide an A-scan free the undesired artifacts.

16. The SDOCT interferometer of claim 15, wherein the variable phase modulator is positioned in one of the reference arm or the sample arm.

17. The SDOCT interferometer of claim 15, wherein the variable phase modulator comprises a switchable phase/polarization modulator.

18. The SDOCT interferometer of claim 15, wherein the variable phase modulator comprises a piezoelectric transducer associated with a mirror.

19. The SDOCT interferometer of claim 15, wherein the variable phase modulator comprises an electro-optic, acousto-optic or photoelastic modulator.

20. The SDOCT interferometer of claim 15, wherein the variable phase modulator comprises:
a phase modulator; and
a driver coupled to the phase modulator and configured to provide signal and power to the phase modulator.

21. The SDOCT interferometer of claim 20, wherein the driver includes:
a function generator coupled to the phase modulator;
a switching amplifier coupled to the function generator; and
a power supply coupled to the switching amplifier.

22. The SDOCT interferometer of claim 21, wherein the function generator is configured to provide:
a tunable sine wave frequency having a range from about 1.0 Hz to about 1.0 MHz and a resolution of at least about 0.004 Hz;
a Continuous phase variation from about 0.0 to about 360 degrees and a degree resolution of at least about 0.09; and/or
a peak to peak voltage amplitude of from about 0.0 to about 20.0 V and a resolution of at least about 20.0 mV.

23. The SDOCT interferometer of claim 21, wherein the function generator is configured to use a direct digital synthesis (DDS) integrated circuit.

24. The SDOCT interferometer of claim 21, wherein the power supply comprises a Class D switching amplifier, a small value resistor in series with the phase modulator and/or a low pass filter.

25. The SDOCT interferometer of claim 21, wherein the power supply comprises a half-bridge switching amplifier.

26. The SDOCT interferometer of claim 15, further configured to integrate over more than three sequential continuous phase shifts.

27. The SDOCT interferometer of claim 15, further configured to integrate over less than three sequential continuous phase shifts.

28. A Fourier domain optical coherence tomography (FDOCT) interferometer comprising a variable phase modulator configured to introduce a variable phase delay between a reference arm and a sample arm of the FDOCT interferometer using continuous phase modulation, wherein the FDOCT interferometer comprises a Spectral domain optical coherence tomography (SDOCT) interferometer, the SDOCT interferometer being further configured to:

introduce a variable phase delay between a reference arm and a sample arm of the SDOCT interferometer using sinusoidal continuous phase modulation;

shift a phase in one of the reference arm or the sample arm sinusoidally in a repetitive manner;

integrate a spectral interferometric signal over four evenly spaced sequential quarter periods of the sinusoidal continuous phase modulation to provide a complex spectral interferogram; and inverse transform the complex spectral interferogram to provide an A-scan free of undesired artifacts.

29. The SDOCT interferometer of claim 28, further configured to integrate over more than four quarter periods.

30. The SDOCT interferometer of claim 28, further configured to integrate over less than four quarter periods.

31. A computer program product removing undesired artifacts in Fourier domain optical coherence tomography (FDOCT) systems using continuous phase modulation, the computer program product comprising:
computer readable storage medium having computer readable program code embodied in the medium, the computer readable program code comprising:
computer readable program code configured to introduce a variable phase delay between a reference arm and a sample arm of an FDOCT interferometer using continuous phase modulation;
computer readable program code configured to generate two or more spectral interferograms having different phase delay integration times; and
computer readable program code configured to combine the spectral interferograms using signal processing to remove undesired artifacts.

32. The computer program product of claim 31, wherein FDOCT comprises Spectral domain optical coherence tomography (SDOCT).

33. The computer program product of claim 32, wherein the undesired artifacts comprise DC, autocorrelation and/or complex conjugate artifacts.

34. The computer program product of claim 32, wherein continuous phase modulation comprises linear continuous phase modulation.

35. The computer program product of claim 34, further comprising:
computer readable program code configured to shift a phase in the reference arm or the sample arm linearly over a round trip delay of $2\phi=2\pi$ radians;
computer readable program code configured to integrate a spectral interferometric signal over three out of four evenly spaced sequential continuous phase shifts of $2\phi=\pi/2$ radians to provide a complex spectral interferogram; and
computer readable program code configured to inverse transform the complex interferogram to provide an A-scan free the undesired artifacts.

36. The computer program product of claim 35, wherein the computer readable program code configured to integrate further comprises computer readable program code configured to integrate over more than three sequential continuous phase shifts.

37. The computer program product of claim 35, wherein the computer readable program code configured to integrate further comprises computer readable program code configured to integrate over less than three sequential continuous phase shifts.

38. The computer program product of claim 32, wherein continuous phase modulation comprises sinusoidal continuous phase modulation.

39. The computer program product of claim 38, further comprising:
  computer readable program code configured to shift a phase in one of the reference arm or the sample arm sinusoidally in a repetitive manner;
  computer readable program code configured to integrate a spectral interferometric signal over four evenly spaced sequential quarter periods of the sinusoidal continuous phase modulation to provide a complex spectral interferogram; and
  computer readable program code configured to inverse transform the complex spectral interferogram to provide an A-scan free of undesired artifacts.

40. The computer program product of claim 39, wherein the computer readable program code configured to integrate further comprises computer readable program code configured to integrate over more than four quarter periods.

41. The computer program product of claim 39, wherein the computer readable program code configured to integrate further comprises computer readable program code configured to integrate over less than four quarter periods.

* * * * *

UNITED STATES PATENT AND TRADEMARK OFFICE
CERTIFICATE OF CORRECTION

| | | |
|---|---|---|
| PATENT NO. | : 7,742,174 B2 | Page 1 of 1 |
| APPLICATION NO. | : 11/778854 | |
| DATED | : June 22, 2010 | |
| INVENTOR(S) | : Izatt et al. | |

It is certified that error appears in the above-identified patent and that said Letters Patent is hereby corrected as shown below:

In the Claims:
Column 17, Claim 15, Line 6: Please correct "signal out of"
                                      to read -- signal over three out of --

Signed and Sealed this
Fourth Day of January, 2011

David J. Kappos
*Director of the United States Patent and Trademark Office*

UNITED STATES PATENT AND TRADEMARK OFFICE
CERTIFICATE OF CORRECTION

PATENT NO. : 7,742,174 B2  Page 1 of 1
APPLICATION NO. : 11/778854
DATED : June 22, 2010
INVENTOR(S) : Izatt et al.

It is certified that error appears in the above-identified patent and that said Letters Patent is hereby corrected as shown below:

On Title Page:
(56) References Cited, Page 2, Foreign Patent Documents:
Please correct "2008/016434 A1   2/2008"
to read -- 2006/016434   2/2006 --

Signed and Sealed this
Fourth Day of September, 2012

David J. Kappos
Director of the United States Patent and Trademark Office